United States Patent [19]

Partika

[11] Patent Number: 5,344,408
[45] Date of Patent: Sep. 6, 1994

[54] BREAK-AWAY SAFETY SHIELD FOR NEEDLE CANNULA

[75] Inventor: Lawrence Partika, Bridgewater, N.J.

[73] Assignee: Becton, Dickinson and Company, Franklin Lakes, N.J.

[21] Appl. No.: 102,874

[22] Filed: Aug. 6, 1993

[51] Int. Cl.⁵ ............................................. A61M 5/32
[52] U.S. Cl. ................................. 604/192; 604/198; 604/263
[58] Field of Search ............... 604/192, 110, 198, 263

[56] References Cited

U.S. PATENT DOCUMENTS

| | | | |
|---|---|---|---|
| 4,636,201 | 1/1987 | Ambrose et al. | 604/192 |
| 4,846,811 | 7/1989 | Vanderhoof | 604/263 |
| 4,892,521 | 1/1990 | Laico et al. | 604/192 |
| 4,911,693 | 3/1990 | Paris | 604/192 |
| 4,929,241 | 5/1990 | Kulli | 604/192 |
| 4,955,866 | 9/1990 | Corey | 604/192 |
| 4,964,866 | 10/1990 | Szwarc | 604/192 |
| 4,981,476 | 1/1991 | Aichlmayr et al. | 604/192 |
| 4,986,817 | 1/1991 | Code | 604/192 |
| 5,053,017 | 10/1991 | Chamuel | 604/192 |
| 5,085,648 | 2/1992 | Purdy et al. | 604/198 |
| 5,171,229 | 12/1992 | McNeil et al. | 604/192 |

FOREIGN PATENT DOCUMENTS 90 00031  8/1990  PCT Int'l Appl. .

*Primary Examiner*—John G. Weiss
*Attorney, Agent, or Firm*—John L. Voellmicke

[57] ABSTRACT

A safety shield assembly is provided for safely enclosing a needle cannula. The safety shield assembly includes an inner shield that is slidably movable along the needle cannula. The inner shield includes a locking structure which locks the inner shield with respect to the distal end of the needle cannula. The safety shield assembly also includes an outer shield that is in releasable engagement with the inner shield. The outer shield will separate from the inner shield in response to excessive force exerted thereon, and hence avoids failure of the structure locking the inner shield to the needle cannula.

17 Claims, 10 Drawing Sheets

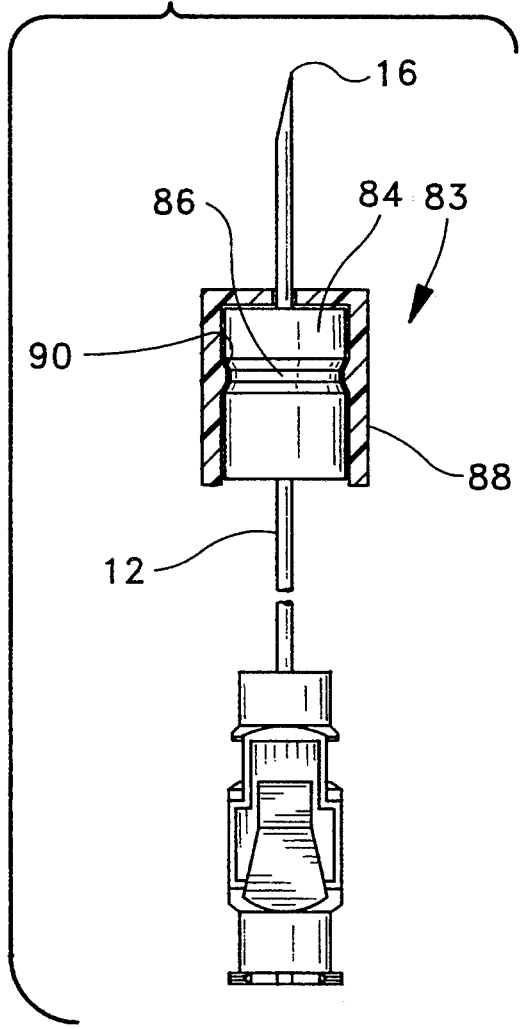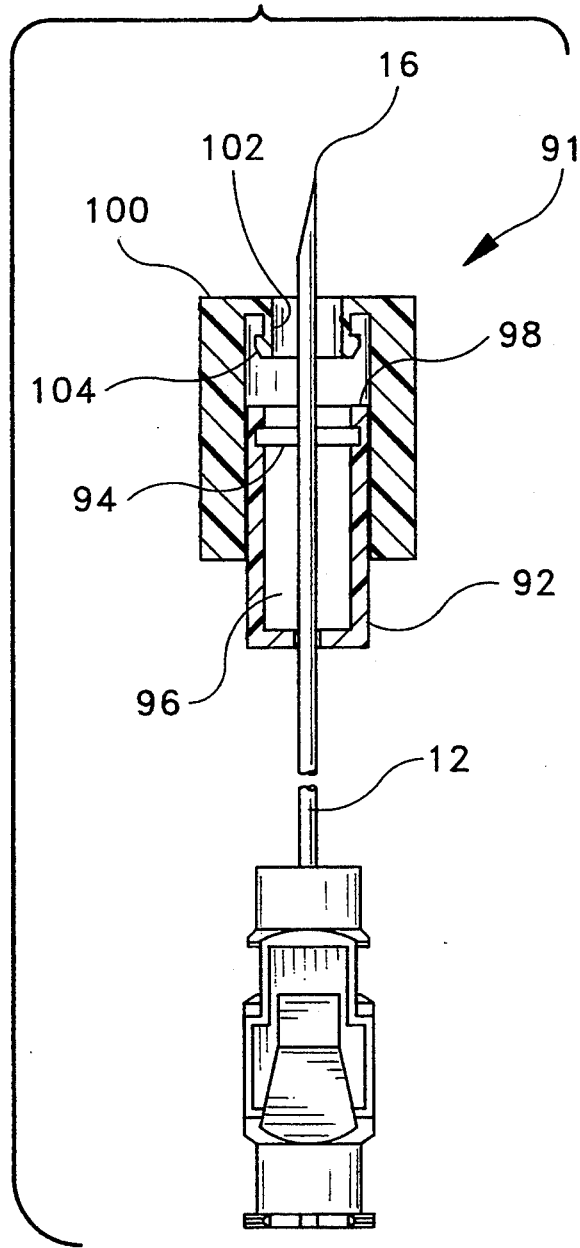

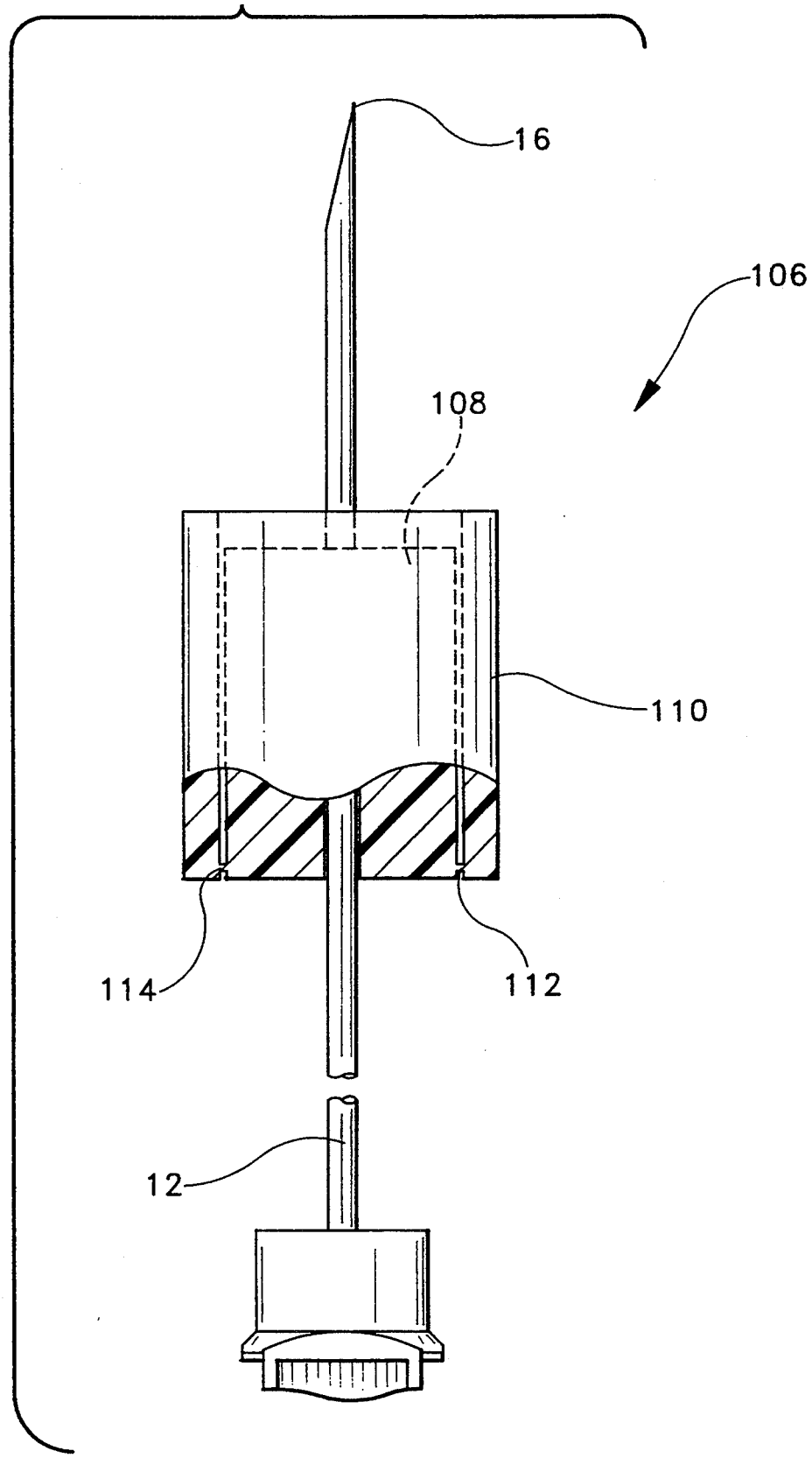

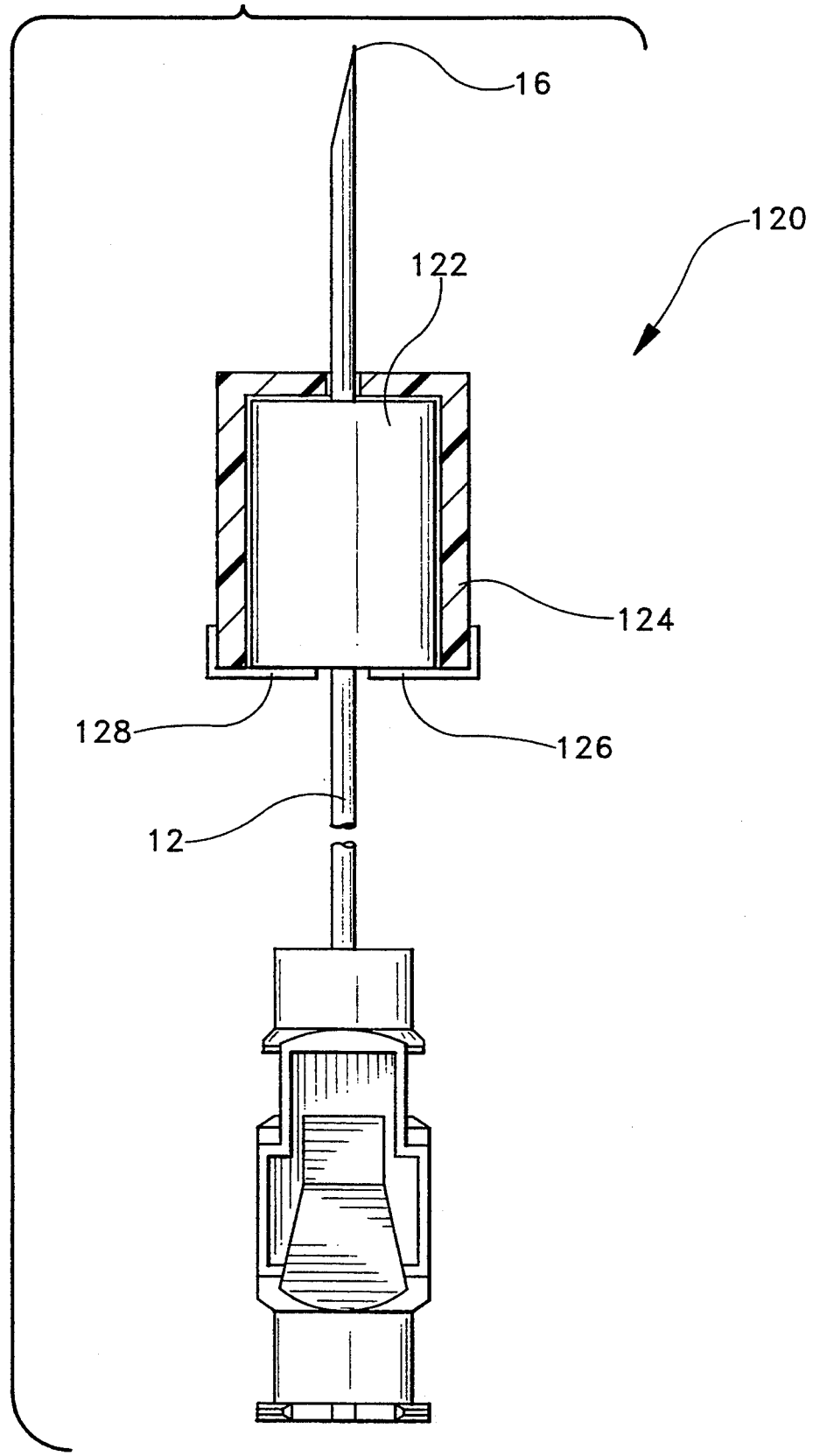

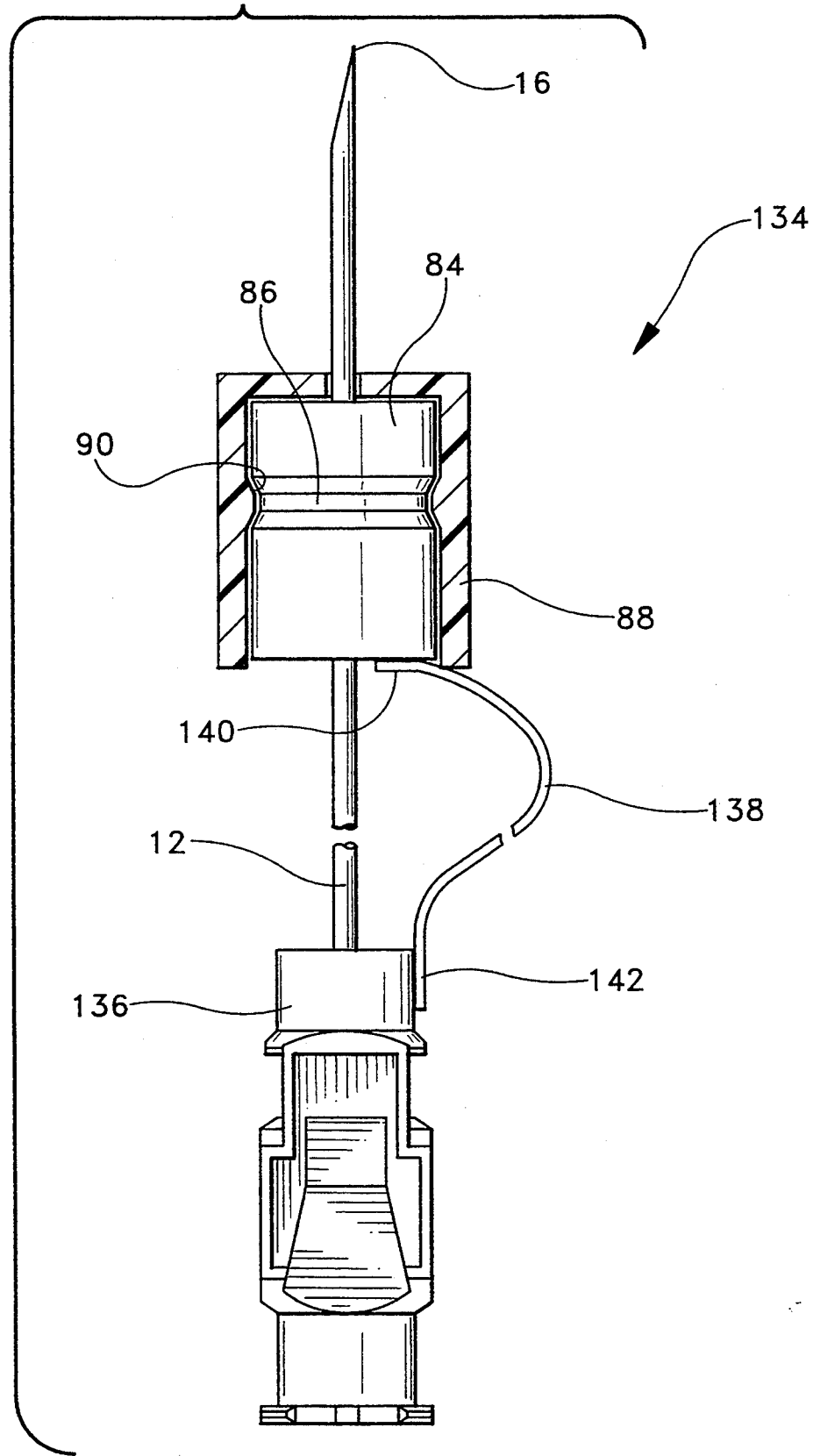

BREAK-AWAY SAFETY SHIELD FOR NEEDLE CANNULA

FIELD OF THE INVENTION

The subject invention relates to safety shields that are axially movable along a needle cannula from a proximal position where the tip of the needle cannula is exposed to a distal position where the tip of the needle cannula is protectively enclosed.

DESCRIPTION OF THE PRIOR ART

The prior art hypodermic syringe includes an elongate barrel having an open proximal end, a distal end and a fluid receiving chamber therebetween. The distal end of the prior art syringe barrel defines a tip having a fluid passage extending therethrough and communicating with the chamber. A plunger may be slidably disposed in the open proximal end of the syringe barrel for urging fluid through the passage in the tip.

A needle cannula can be mounted to the distal end of the prior art syringe barrel. The needle cannula has a proximal end, a sharp distal end and a lumen extending therebetween. The proximal end of the needle cannula is secured to a mounting hub that can be engaged on the distal end of the syringe barrel such that the passage through the distal end of the syringe barrel communicates with the lumen through the needle cannula.

The prior art needle cannula is prepackaged in a needle shield to prevent accidental needle sticks prior to the first intended use of the needle cannula. The shield can be removed after the needle cannula has been mounted to the syringe barrel and immediately prior to use. A health care worker then uses the unshielded needle cannula and hypodermic syringe to either inject medication into a patient or to withdraw bodily fluid for subsequent diagnostic evaluation.

Needle sticks that occur before the hypodermic syringe is used create less risk of infection because the needle is sterile. However, needle sticks occurring after the hypodermic syringe has been used pose a greater risk of infection or disease transmission. As a result, the prior art includes shields for protectively enclosing at least the tip of the used needle cannula.

Some prior art shields define a separate cap that can be telescoped in a proximal direction over the used needle cannula. However, separate caps often are lost or misplaced in the hectic environment of a medical facility. Additionally, the movement of the used needle cannula and the separate cap toward one another creates the potential for an accidental needle stick.

The prior art also includes needle shields that cannot be misplaced and that are intended to avoid the movement of one hand toward the other during a shielding operation. Needle shields of this type typically are releasably retained near the proximal end of the needle cannula. The distal end of the needle cannula is exposed and can be used in the standard manner. After use, however, the prior art needle shield can be slid distally along the needle cannula and into a shielding position.

The prior art needle shield of this type typically includes means for lockingly engaging the needle cannula when the distal tip has been reached. The locking is intended to prevent further movement of the prior art shield in either a distal direction or a proximal direction. Distally directed movement of the locked prior art needle shield in some prior art devices is prevented by frictional or spring biased engagement of the shield with the smooth outer cylindrical surface of the needle cannula. Prior art shields of this general type are shown, for example, in: U.S. Pat. No. 4,929,241; U.S. Pat. No. 5,053,017 and WIPO Publication PCT/CA90/00031. Other prior art needle shields lockingly engage a discontinuity along the length of the needle cannula as shown in U.S. Pat. No. 4,846,811.

Prior art needle shields of the type described above can be designed to exert significant locking forces against the exterior surface of the needle cannula. However, all such prior art needle shields will have some limit to their locking force. The locking force will be limited by the design and will vary with the dimensional tolerances of the shield components. Thus, separation of the needle shield from the needle cannula can occur if the forces exceed the maximum locking force between the prior art needle shield and the needle cannula. Needle shields desirably should be as small as possible. However, smaller needle shields will exert lower gripping forces, and hence are more easily separated from the needle cannula.

Separation of a prior art needle shield from a needle cannula may not require abusive use of the hypodermic syringe. Rather, separation can occur inadvertently if a health care worker exerts too much force in an effort to shield the needle cannula. Separation of the needle shield is accompanied by a sudden recognizable reduction in engagement forces between the shield and the needle cannula. The automatic reaction by the health care worker who inadvertently caused the separation is to attempt an immediate re-shielding by urging the shield back in a proximal direction. This is precisely the movement that shields of this type are intended to avoid. Under these circumstances, the re-shielding attempt will be an abrupt reactionary movement that can easily generate an accidental needle stick with a potentially contaminated needle.

SUMMARY OF THE INVENTION

The subject invention is directed to a safety shield assembly. The safety shield assembly includes a rigid inner shield that slidably moves in response to a force $F_s$ from a proximal position on a needle cannula to a distal position where the tip of the needle cannula is safely shielded. The inner shield may include means for sensing the distal end of the needle cannula and means for securely gripping the needle cannula when the distal tip of the needle cannula has been shielded. The locked inner shield may be prevented from a return or proximal movement along the needle cannula, and will move further distally only in response to a relatively great failure force $F_f$.

The safety shield assembly also includes an outer shield substantially surrounding the inner shield. The outer shield is releasable engaged with the inner shield, and can be separated or broken from the inner shield in response to a breakaway force $F_b$. The inner and outer shields are designed such that the breakaway force, $F_b$, is greater than the force $F_s$ required to slide the inner safety shield along the needle cannula, but less than the force $F_f$ required to separate the inner shield from the needle cannula.

In most instances the health care worker will never know that the safety shield assembly includes two components. More particularly, the health care worker will merely grasp the outer shield in a standard manner, and will exert a force equal or slightly greater than $F_s$ to slide the inner shield distally along the needle cannula. This force exerted by the health care worker typically will be less than the breakaway force $F_b$ required to separate the outer shield from the inner shield. However, if the health care worker inadvertently or incorrectly exerts an excessive force on the safety shield assembly, the outer shield will separate from the inner shield when the breakaway force $F_b$ is reached and well prior to the time when the failure force $F_f$ is reached. Thus, such excessive force will merely separate the outer shield from the inner shield after locking has been achieved. The inner shield will remain safely in place in surrounding relationship to the distal tip of the needle cannula.

BRIEF DESCRIPTION OF THE DRAWINGS

FIG. 10 is a cross-sectional view similar to FIG. 2, but showing an alternate engagement between the inner and outer shields.

FIG. 11 is a cross-sectional view similar to FIG. 10, but showing another alternate engagement between the inner and outer shield.

FIG. 12 is a cross-sectional view substantially similar to the embodiment of FIG. 10 with frangible links connecting the inner shield and the outer shield.

FIG. 13 is a cross-sectional view substantially similar to the embodiment of FIG. 10 with frangible sheet material connecting the inner shield and the outer shield.

FIG. 14 is a cross-sectional view substantially similar to the embodiment of FIG. 10 with the addition of a flexible link connecting the inner shield and the hub.

DETAILED DESCRIPTION OF THE PREFERRED EMBODIMENTS

Figure 1:
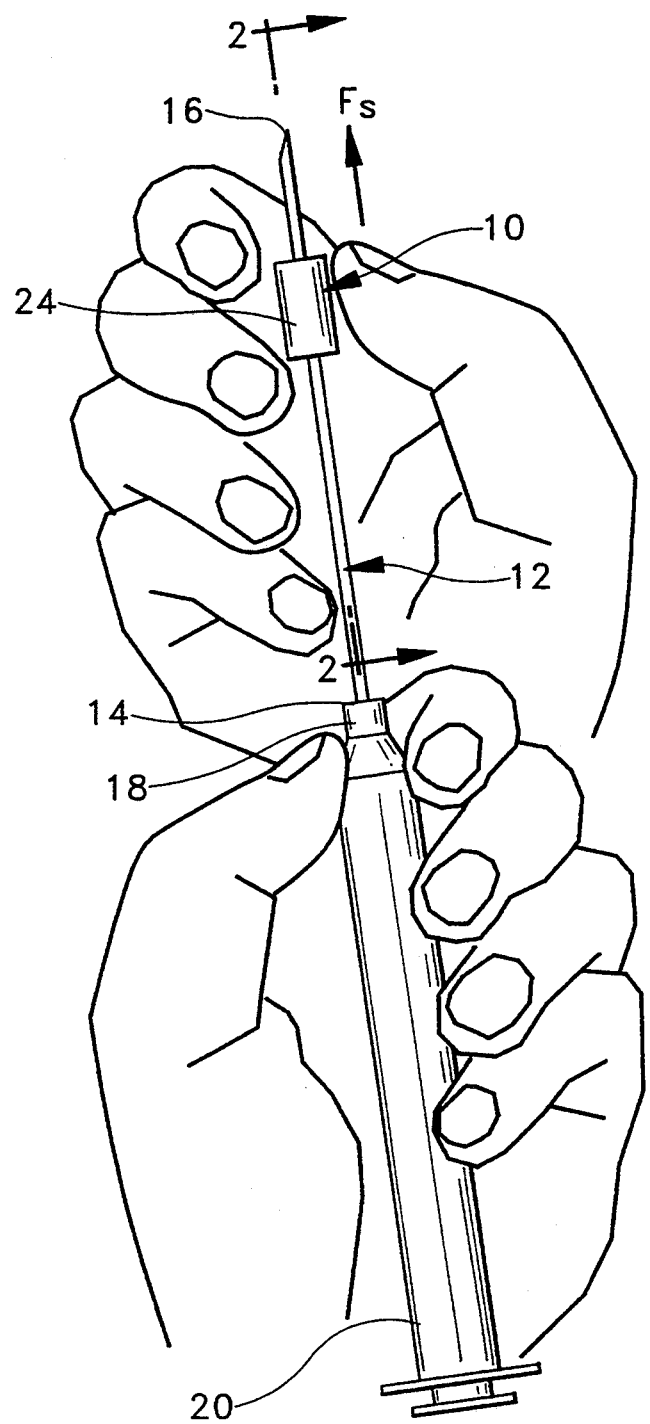
FIG. 1 is a perspective view of a hypodermic syringe and a safety shield in accordance with the subject invention.

A safety shield assembly in accordance with the subject invention is identified generally by the numeral 10 in FIGS. 1–5. Safety shield assembly 10 is slidably disposed on a needle cannula 12 having a proximal end 14, a sharp distal tip 16 and a lumen extending therebetween. Proximal end 14 of needle cannula 12 is securely mounted to a hub 18 which is threadedly engageable with a hypodermic syringe 20.

Safety assembly 10 initially is releasably engaged or positioned near proximal end 14 of needle cannula 12. However, safety shield assembly 10 can be slid distally in response to force $F_s$ exerted thereon by a thumb and forefinger as shown in FIG. 1.

Figure 2:
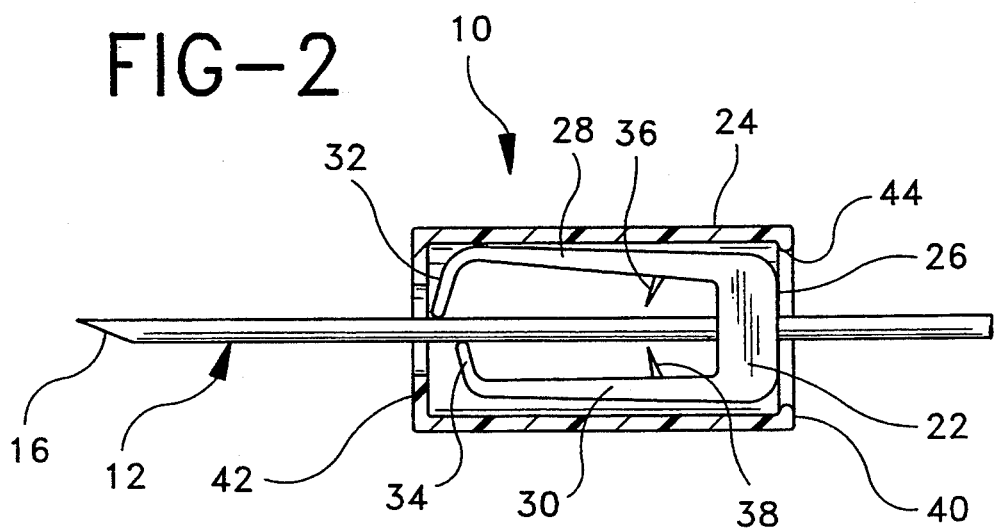
FIG. 2 is a cross-sectional view taken along line 2—2 in FIG. 1.
Figure 3:
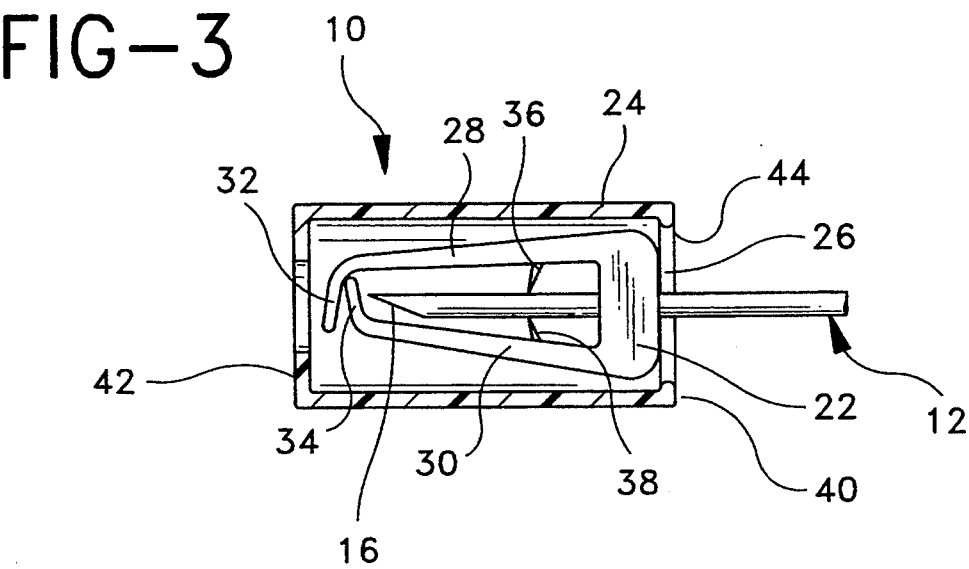
FIG. 3 is a cross-sectional view similar to FIG. 2, but showing the needle cannula and safety shield assembly in a fully shielded condition.
Figure 4:
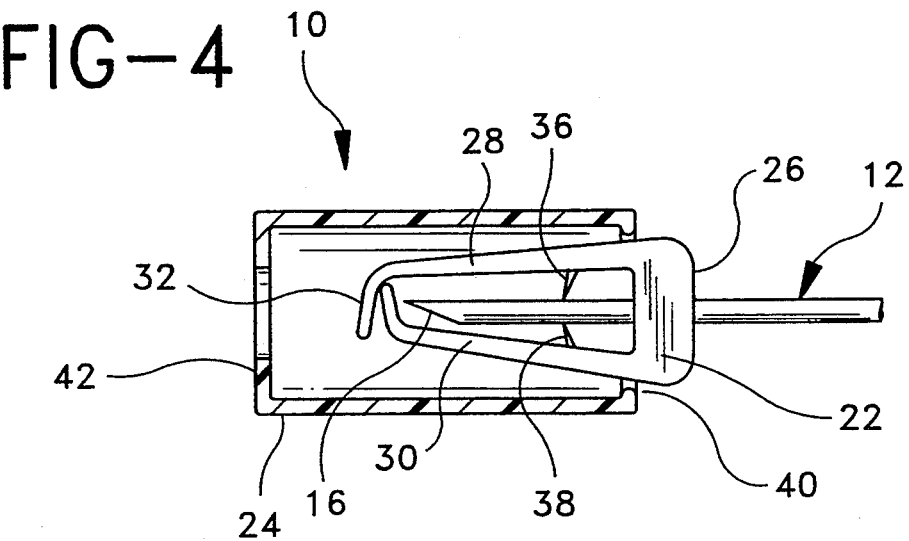
FIG. 4 is a cross-sectional view similar to FIGS. 2 and 3, but showing the outer shield partly disengaged from the inner shield.

Safety shield assembly 10 includes an inner shield 22 and an outer shield 24 releasably engaged over the inner shield 22. The inner shield may take any of several different forms. As shown in FIGS. 2–4, inner shield 22 is substantially similar to the shield depicted in the above-referenced U.S. Pat. No. 4,929,241. More particularly, the proximal end of inner shield 22 defines a base 26 slidably mounted over needle cannula 12. Lever arms 28 and 30 project distally from base 26 and include inwardly directed ends 32 and 34 respectively. As shown in FIG. 2, ends 32 and 34 are in sliding engagement with the outer cylindrical surface of needle cannula 12. In this condition lever arms 28 and 30 respectively are preloaded away from needle cannula 12. Lever arms 28 and 30 further include locking teeth 36 and 38 respectively which project inwardly toward needle cannula 12 from locations intermediate the respective lengths of lever arms 28 and 30. Locking teeth 36 and 38 are dimensioned to be spaced from needle cannula 12 when ends 32 and 34 of lever arms 28 and 30 are in sliding engagement with needle cannula 12.

Outer shield 24 is preferably a generally cylindrical structure having opposed proximal and distal ends 40 and 42 respectively. Outer shield 24 preferably defines an axial length greater than the corresponding axial length of inner shield 22. Thus, inner shield 22 is substantially inaccessible, and outer shield assembly 24 will define the region of all manual contact with shield assembly 10.

Proximal end 40 of outer shield 24 includes a radially inwardly extending flange 44 which is dimensioned to releasably engage radial outer portions of base 26 at the proximal end of inner shield 22. Flange 44 will separate from inner shield 22 if relative forces between inner and outer shields 22 and 24 approach the breakaway force, $F_b$.

Distally directed forces of $F_s$ exerted on outer shield 24 will cause an initial sliding movement of the entire shield assembly 10 distally indicated as direction "A" in FIG. 1, without separating outer shield 24 from inner shield 22. Sufficient distal movement of shield assembly 10 will cause ends 32 and 34 of lever arms 28 and 30 to pass beyond distal end 16 of needle cannula 12. The preload referred to above will cause arms 28 and 30 to resiliently return toward an undeflected condition, such that ends 32 and 34, protectively enclose distal tip 16 of needle cannula 12 to prevent proximal movement of the needle shield, and such that teeth 36 and 38 grippingly engage the outer circumferential surface of needle cannula 12 to help prevent further distal movement of the needle shield.

Figure 5:
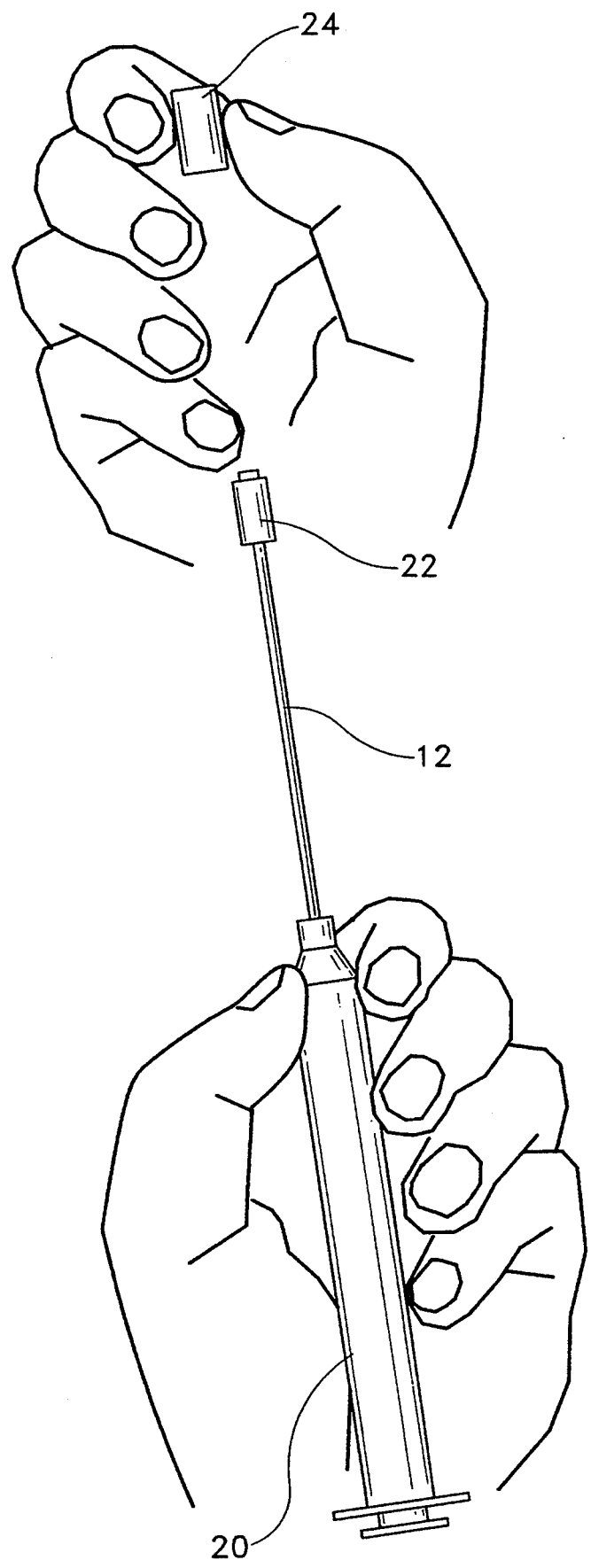
FIG. 5 is a perspective view similar to FIG. 1 but showing the outer shield fully separated from the inner shield.

Most health care workers will detect the locking of shield assembly 10 to needle cannula 12 and will stop their exertion of axial forces thereon. However, inexperienced health care workers or workers distracted by exigencies of a medical facility may continue to exert axial forces on shield assembly 10 after the FIG. 3 locked engagement has been achieved. Inner shield 22 will resist distally directed force up to a force $F_f$ beyond which failure of the locked engagement to needle cannula 12 will occur. However, the breakaway force $F_b$ between inner and outer shields 22 and 24 is less than failure force $F_f$. Hence, continued exertion of distally directed axial force on outer shield 24 after the locked FIG. 3 position has been achieved will merely cause flange 44 to disengage from inner shield 22 as shown in FIG. 4. Continued force will cause the complete separation of outer shield 24 from inner shield 22 as shown in FIG. 5. However, inner shield 22 will remain protectively engaged in shielding relationship to distal point 16 of needle cannula 12 substantially as shown in FIGS. 3 and 4. Thus, even if the health care worker appreciates his or her error and attempts to re-shield needle cannula 12, an accidental needle stick will be positively prevented by the continued gripping engagement of inner shield 22 with needle cannula 12.

Figure 6:
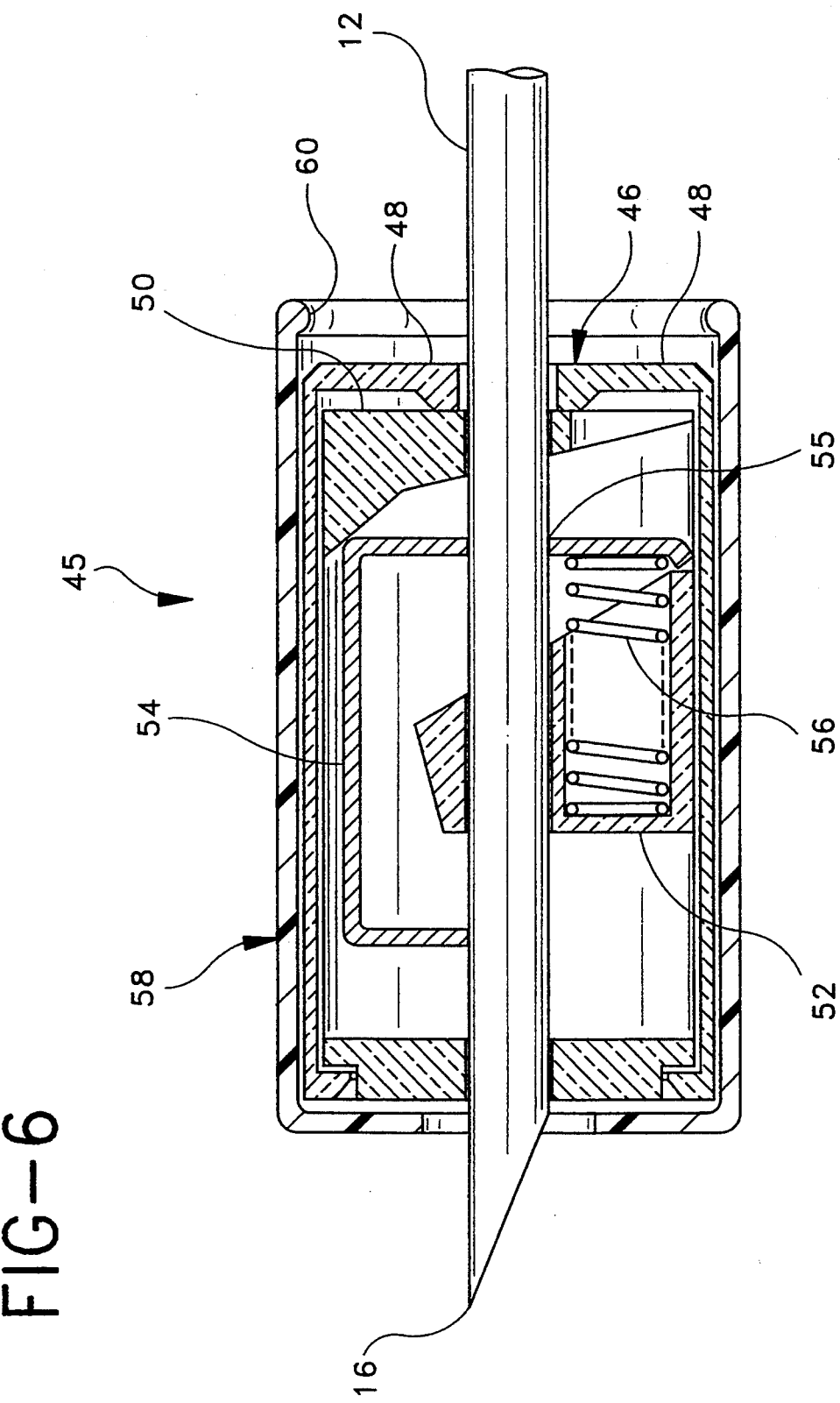
FIG. 6 is a cross-sectional view similar to FIG. 2, but showing a second embodiment of an inner shield.
Figure 7:
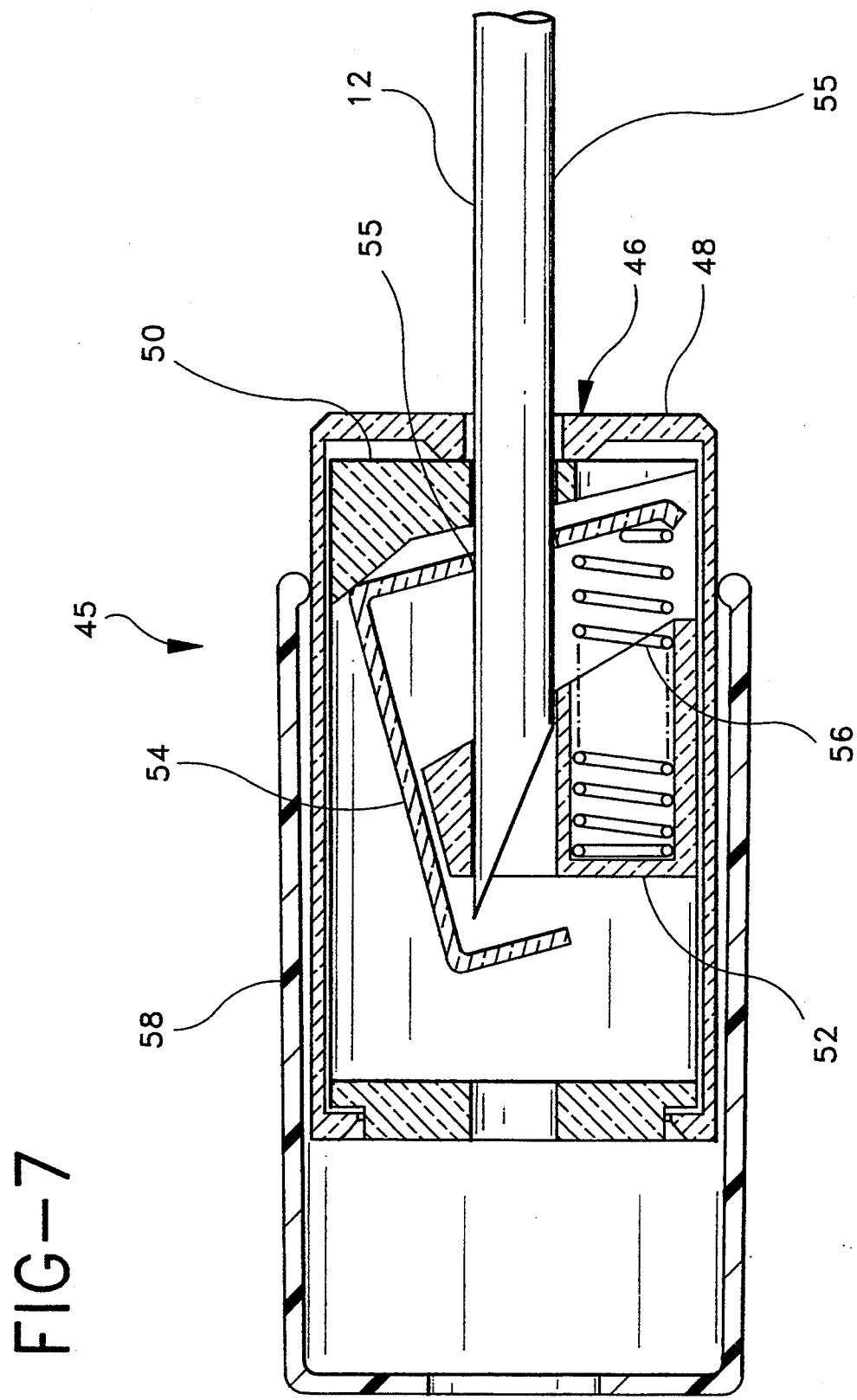
FIG. 7 is a cross-sectional view showing the inner shield of FIG. 6 shielding the cannula tip of the outer shield partially disengaged from the inner shield.

The inner shield can take many other optional configurations for protectively enclosing distal tip 16 of needle cannula 12. For example, in FIG. 6, a shield assembly 45 having an inner shield 46 substantially as shown in WIPO Publication No. PCT/CA90/0031. More particularly, inner shield 46 in FIGS. 6 and 7 includes an inner shield housing 48 which contains a wedge actuator 50 in clipping engagement over needle cannula 12. A biased actuator 52 also is slidably mounted to needle cannula 12 in a position distally of wedge actuator 50. Clamp 54 is in sliding engagement with needle cannula 12 at a first location intermediate wedge actuator 50 and biased actuator 52, and at a second position distally of biased actuator 52. Clamp 54 also is engaged by wedge actuator 50. A coil spring 56 extends between biased actuator 52 and clamp 54. Spring 56 will cause clamp 54 to rotate counter clockwise as shown in FIG. 7. This rotation will cause the distal end of clamp 54 to protectively enclose distal tip 16 of syringe barrel 12, and will simultaneously cause proximal portions of clamp 54 inside aperture 55 in the clamp to grippingly engage needle cannula 12. Wedge actuator 50 will drive clamp 54 into tighter clamping engagement in response to distally directed axially forces exerted on inner shield 46. As noted above, some force $F_f$ will exist beyond which failure of inner shield 46 will occur. Outer shield 58 prevents such failure from occurring. More particularly, outer shield 58 substantially completely encloses inner shield 46 to prevent direct manual contact with any portion of inner shield 46. Outer shield 58 also includes a ridge 60 for releasably griping the proximal end of inner shield 46. Outer shield 58 will separate from inner shield 46 in response to a breakaway force $F_b$ which exceeds the force required to slidably move the entire shield assembly along needle cannula 123, but which is less than the failure force $F_f$. Thus, the shield assembly shown in FIGS. 6 and 7 will function substantially the same as the shield assembly of FIGS. 2–4 despite the significantly different construction of the inner shield.

Figure 8:
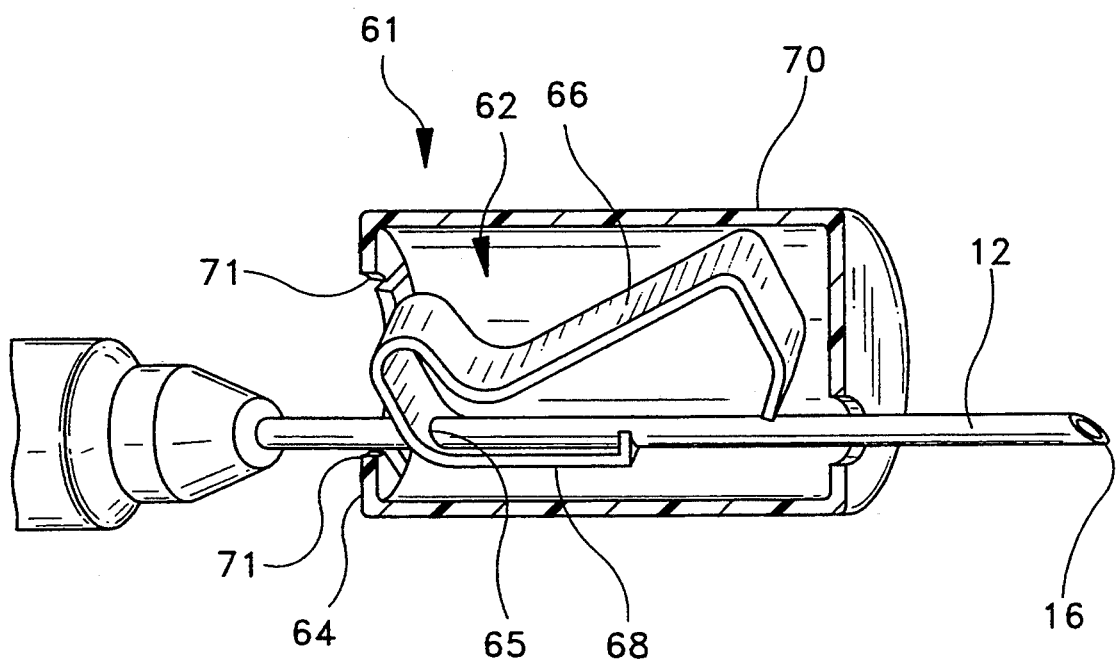
FIG. 8 is a perspective view, partly in section, showing a third embodiment of inner and outer shields disposed in the retracted needle tip exposing position on a needle cannula.

A third safety shield assembly that will perform similarly to the shield assemblies of FIGS. 1–7, is shown in FIG. 8, and is identified generally by the numeral 61. Shield assembly 61 includes an inner shield 62 substantially as disclosed in U.S. Pat. No. 5,053,017. More particularly, inner shield 62 is stamped and formed from a unitary strip of spring metal and includes a proximally disposed base 64 having an aperture 65 for slidably engaging needle cannula 12. Arms 66 and 68 extend from base 64 and include ends which are in sliding contact with the needle cannula. Arm 66 is preloaded and biased away from needle cannula 12. Then, when the end of arm 66 aligns with distal tip 16 of needle cannula 12, arm 66 will resiliently return toward an undeflected condition, such that the end thereof protectively encloses distal tip 16 of needle cannula 12. Simultaneously, needle cannula 12 will be securely gripped by base 64 in the area of aperture 65. Shield assembly 61 further includes an outer shield 70 having inwardly facing cantilever members 71 capable of releasably engaging the inner shield 62. Outer shield 70 will separate from inner shield 62 in response to a breakaway force $F_b$ which is greater than the force $F_s$ required to slide inner shield 62 along needle cannula 12. In this embodiment the breakaway force is the force required to deflect the cantilevers 71 as they pass over the largest portion of the inner shield. However, as in the previous embodiment, breakaway force $F_b$ to separate outer shield 70 from inner shield 62 is less than the force $F_f$ that will cause failure of inner shield 62 on needle cannula 12.

Figure 9:
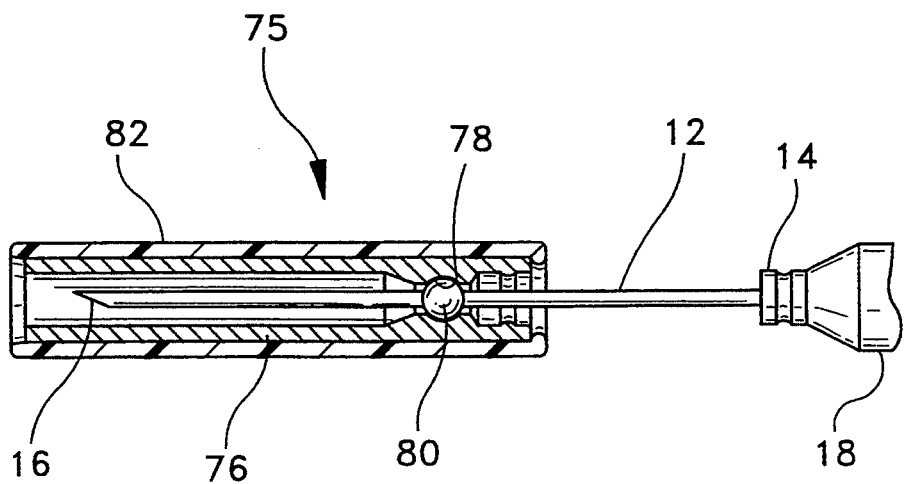
FIG. 9 is a cross-sectional view showing a fifth embodiment of the inner shield and outer shields.

The embodiments of the subject invention described and illustrated above all rely upon an inner shield 22, 46, 62 grippingly engaging a needle cannula. Some prior art safety shields attempt to enhance shielding effectiveness by providing physical structure to help prevent further distal motion of the shield, such as a discontinuity along the length of the needle cannula, or a notch may be formed in a needle cannula for gripping engagement by locking means on a shield. Also, a flexible link of plastic may connect the shield and the hub as illustrated in FIG. 14. Similarly, a bead of material may be disposed at a selected axial position along the needle cannula for engagement by the shield. These structures on the needle cannula are intended to prevent complete separation of the shield therefrom. However, as noted above, all such shields will fail in response to some application of excess force even if the shield does not move from the needle the needle may be pulled out of the needle hub or the needle hub may be pulled out of the syringe barrel. The combination of inner and outer shields as described above can be applied to a needle cannula having engagement discontinuities thereon. For example, a needle shield assembly 75 is shown in FIG. 9, and includes an inner shield 76 substantially similar to the shield shown in U.S. Pat. No. 4,8456,811. Inner shield 76 includes an annular engagement groove 78 for engaging a bead 80 on the needle cannula 12. Shield assembly 10c further includes an outer shield 82 releasably engaged with inner shield 76. As in the previous embodiments, outer shield 82 will separate from inner shield 76 in response to a breakaway force $F_b$ which is greater than the force $F_s$ required to slide inner shield 76 along needle cannula 12, but less than the failure force $F_f$ required to separate inner shield 76 from annular bead 80 on needle cannula 12.

The embodiments described and illustrated above all included engagement means on the proximal end of the outer shield for releasably engaging the proximal end of the inner shield. Variations of this engagement are possible, and are shown schematically in FIGS. 10 and 11. More particularly, FIG. 10 shows a shield assembly 83 having an inner shield 84 with an annular groove 86 intermediate its length. Inner shield 84 may include locking means as shown in some of the above described embodiments. Shield assembly 83 further includes an outer shield 88 having an inwardly extending annular bead 90, or separate inwardly directed projections, releasably engaged in annular groove 86 of inner shield 84. As in the previous embodiments, outer shield 88 will separate from inner shield 84 in response to a breakaway force $F_b$ which is greater than the force $F_s$ required to slide the inner shield 84 along the needle cannula 12, but less than the failure force $F_f$ at which the locking structure of the inner shield 84 to the needle cannula fails.

FIG. 11 shows a shield assembly 91 where an inner shield 92 includes an annular locking groove 94 on an inwardly facing surface 96 near distal end 98. An outer shield 100 has a proximally projecting sleeve 102 with a locking bead 104 for releasable engagement in groove 94 of inner shield 92. As in the previous embodiments, outer shield 100 will separate from inner shield 92 in response to a breakaway force $F_b$ which is greater than the force $F_s$ required to slide inner shield 92 axially along needle cannula 12, but less than the force $F_f$ at which the locking mechanism of inner shield 92 fails.

It is also within the purview of the instant invention to include connecting the inner shield and the outer shield by a frangible link or a plurality of frangible links, as illustrated in FIG. 12. FIG. 12 shows shield assembly 106 consisting of inner shield 108 connected to outer shield 110 through integrally molded frangible links 112 and 114. The links may be formed by integrally molding the inner and outer shields at the same time. The frangible connection may be provided by connecting the inner and outer shields with adhesive-backed laminated sheet material, such as paper label stock or plastic sheet, designed to fracture at a preselected $F_b$. FIG. 13 illustrates such an embodiment. In FIG. 13 shield assembly 120 consists of inner shield 122 and outer shield 124 connected by laminated adhesive-backed paper strips 126 and 128. Flexible links may also be molded on one of the shields and attached to the other shield using adhesive, mechanical joining, ultrasonic welding or the like. FIG. 14 illustrates shield assembly 134 which is identical in all respects to shield assembly 83 of FIG. 10, except that in the shield assembly of FIG. 14 inner shield 84 is connected to needle hub 36 through a flexible link 138. In this embodiment flexible link 138 is made of plastic and is connected to inner shield 84 at 140 and to needle hub 136 at 142. Flexible link 138 is long enough to allow the inner shield to extend distally to cover needle tip 16 but not far enough to allow inner shield 84 to move distally past distal tip 16 of needle 12.

What is claimed is:

1. A safety shield assembly comprising:
   a needle cannula having a proximal end, a distal end and a lumen therethrough;
   an inner shield slidably movable along said needle cannula from a proximal position at least partially on said needle cannula where said distal end of said needle cannula is exposed, to a distal position at least partially on said needle cannula where said distal end of said needle cannula is shielded;
   locking means for helping to prevent said inner shield from moving distally with respect to said needle cannula when said inner shield is in said distal position on said needle cannula;
   an outer shield disposed in surrounding relationship to said inner shield; and
   means for selectively disengaging said outer shield from said inner shield in response to a distally directed force of a selected magnitude exerted on said outer shield, said distally directed force being less than a force required to move said inner shield distally off the needle cannula, after said inner shield is in said distal position.

2. The safety shield assembly of claim 1, wherein said inner and outer shields each include opposed proximal and distal ends, said outer shield including deflectable locking means adjacent said proximal end for releasably engaging said proximal end of said inner shield.

3. The safety shield assembly of claim 1, wherein said inner shield includes opposed proximal and distal ends and an engagement deformation therebetween, said outer shield including an engagement deformation releasably engageable with said engagement deformation of said inner shield.

4. The safety shield assembly of claim 3, wherein said engagement deformation of said inner shield comprises a recessed annular deformation therein, and wherein said engagement deformation of said outer shield is a projection releasably engageable with said recessed annular deformation of the inner shield.

5. The safety shield assembly of claim 1, wherein the inner shield includes opposed proximal and distal ends and opposed inner and outer surfaces, said inner shield including an engagement deformation on portions of said inner surface adjacent said distal end, said outer shield including opposed proximal and distal ends, said outer shield further comprising engagement means projecting proximally from said distal end for engagement with said engagement deformation of said inner shield.

6. The safety shield assembly of claim 5, wherein said annular deformation of said inner shield comprises an annular groove, the engagement means of said outer shield comprising a deflectable engagement sleeve projecting proximally from said distal end of said outer shield for releasably engaging the groove of said inner shield.

7. The safety shield assembly of claim 1, wherein said needle cannula includes a locking deformation intermediate said proximal and distal ends thereof, said locking means of said inner shield being lockingly engageable with said locking deformation on said needle cannula.

8. The safety shield assembly of claim 1 wherein said means for selectively disengaging said outer shield from inner shield includes a frangible link connecting said outer shield to said inner shield.

9. The safety shield assembly of claim 8 wherein said frangible link is integrally molded to one of said shields.

10. The safety shield assembly of claim 8 wherein said frangible link comprises an adhesive backed sheet connected by said adhesive to said inner shield and said outer shield.

11. The safety shield assembly of claim 1 wherein said locking means is disposed in said inner shield for locking said inner shield to said cannula.

12. The safety shield assembly of claim 11 wherein said locking means includes a deformation on said cannula.

13. The safety shield assembly of claim 12 wherein said deformation is an outwardly extending projection.

14. The safety shield assembly of claim 1 wherein said needle cannula includes a needle hub having a passageway therethrough at said proximal end of said cannula, said lumen and said passageway being in fluid communication.

15. The safety shield assembly of claim 14 wherein said locking means includes a flexible link between said needle hub and said inner shield.

16. The safety shield assembly of claim 1, wherein locking means includes sensing means for sensing said distal end of said needle cannula and for locking said inner shield to said needle cannula upon said sensing of said end of said needle cannula by said sensing means.

17. The needle shield assembly of claim 16, further comprising biasing means for moving said locking means relative to said needle cannula upon sensing of the end of said needle cannula by said sensing means.

* * * * *